United States Patent [19]

Le Page et al.

[11] 4,391,701

[45] Jul. 5, 1983

[54] PROCESS FOR UPGRADING HEAVY OILS

[75] Inventors: Jean-François Le Page, Rueil Malmaison; Germain Martino, Poissy, both of France

[73] Assignee: Institut Francais du Petrole, Rueil-Malmaison, France

[21] Appl. No.: 252,675

[22] Filed: Apr. 9, 1981

[30] Foreign Application Priority Data

Apr. 9, 1980 [FR] France .............................. 80 07956

[51] Int. Cl.$^3$ ........................... C10L 1/02; F17D 1/17
[52] U.S. Cl. .................................... 208/370; 208/950; 137/13; 585/3; 44/54
[58] Field of Search ................. 208/370, 950; 137/13; 44/54, 53, 51; 518/702, 703; 585/3

[56] References Cited

U.S. PATENT DOCUMENTS 3,926,203 12/1975 Marsden, Jr. et al. ............... 137/13
4,027,688 6/1977 Gruber et al. ......................... 137/13
4,122,110 10/1978 Sugier et al. ........................ 252/464

Primary Examiner—Delbert E. Gantz
Assistant Examiner—O. Chaudhuri
Attorney, Agent, or Firm—Millen & White

[57] ABSTRACT

The viscosity of heavy oils is reduced in order to facilitate pipe line transportation thereof. A fraction of the heavy oil is deasphalted in the presence of $C_5$–$C_7$ hydrocarbons, a portion of the separated asphalt is converted to synthesis gas, at least a portion of said gas is used to manufacture an alcohol mixture including methanol and $C_2$ to $C_{10}$ alcohols, which mixture is admixed with the heavy oil before transportation thereof. This procedure is more beneficial to the transported heavy oil than the prior processes which do not comprise the conversion of the asphalt fraction of the heavy oil.

13 Claims, 2 Drawing Figures

PROCESS FOR UPGRADING HEAVY OILS

BACKGROUND OF THE INVENTION

The present invention concerns a series of sequential processes having for object to upgrade highly viscous heavy oils which cannot be transported under the usual conditions through pipe-lines as presently in operation. These heavy oils and more precisely these heavy curde oils are materials whose specific gravity is generally higher than 0.950 and whose viscosity at 70° C. is close to or higher than 1000 centistokes ($10^{-3}$ m$^2$/sec) or materials whose viscosity at 40° C. is close to or higher than 10,000 centistokes ($10^{-2}$ m$^2$/sec) such, for example, as the heavy crude oils from the Athabasca sands or the Orenoque belt. In addition to their high viscosity, these oils are also characterized by a high content of asphaltenes and a very low content of gasoline distilling below 200° C. (or even below 100° C.), particularly this is the case of the heavy crude oils produced in the petroleum fields of the Orenoque belt (these crude oils often do not contain substantially more than to 2% by weight of light gasoline).

In view of their high viscosity, these crude oils cannot be transported as such. Several solutions, already applied to conventional crude residues of high viscosity or to crude oils produced in very cold regions, may obviously be considered, such as a dilution with a light fluxing fluid and/or the maintenance of the oil in the pipe-line at a sufficient temperature to avoid pumping and conveyance problems. Another solution, also suggested, consists of proceeding at the oil well outlet to a minimum refining operation, so as to convert the considered crude oil and to extract therefrom the noble fraction which can be transported without problem. Thus a refining operation, comprising desalting, deasphalting with pentane and visbreaking of the deasphalted oil, provides only for the deasphalted oil, the viscosity required for its pipe-line transportation under at least substantially normal conditions, nonetheless, in this particular case, an unsolved problem is that raised by the asphaltenes present in the solid state which are difficult to transport and must be used to produce vapor or power on the very site of production. Another type of refining, comprising desalting and coking, also provides for the production, on the one hand, of a transportable distillate fraction and on the other hand, of a solid, i.e. coke which can be used, similarly as the asphaltenes in the preceding case, for producing vapor or power on the production field.

OBJECTS OF THE INVENTION

Figure 1:
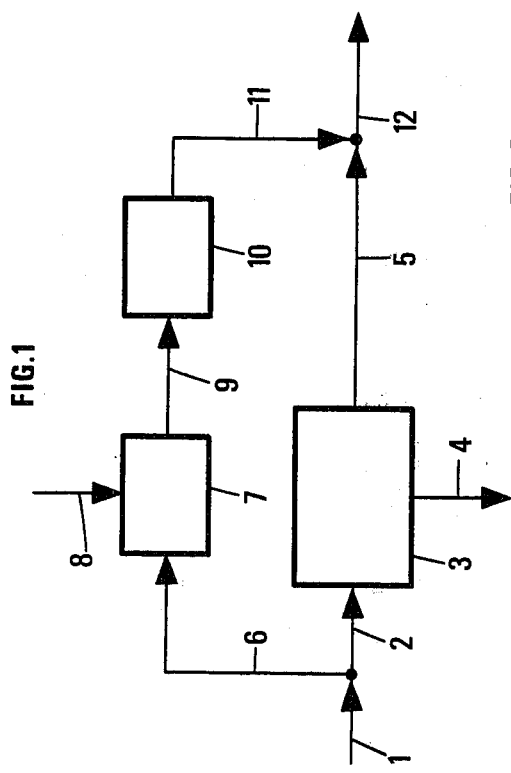
FIG. 1 is a schematic diagram of a prior art process, for comparison.

As compared with these different solutions having for object to make heavy oils of high viscosity more easily transportable, the present invention proposes another solution whereby more value can be added to the heavy oil and particularly to the asphaltic fraction thereof, obtained by deasphalting the crude oil with, for example, pentane or, more generally, a hydrocarbon or a mixture of hydrocarbons comprising from 5 to 7 carbon atoms per molecule.

DETAILED DISCUSSION

The invention concerns a refining process for heavy oils having a very low content of gasoline distilling below about 200° C. and, more particularly, below about 100° C.

The process consists of converting a fraction of the heavy oil to a mixture of alcohols comprising methanol and at least one higher alcohol containing from 2 to 10, more particularly 2 to 5 carbon atoms per molecule, according to a process comprising the following sequence of steps:

At least partial oxidation with oxygen of a fraction of the considered heavy oil to produce a synthesis gas containing CO, $CO_2$, $H_2$ with $H_2S$ and $NH_3$ impurities, purification of said gas for removing the $H_2S$ and $NH_3$ impurities, synthesis, in one or more steps, of alcohols containing from 1 to 10, particularly from 1 to 5 carbon atoms per molecule so as to obtain, at the end of the sequence, a mixture of alcohols comprising, for example, from about 10 to 90% by weight of methanol, more particularly from 60 to 85%, preferably from 10 to 50% or from 15 to 40% of methanol, the remainder, up to 100%, consisting of at least one higher alcohol having, for example, from 2 to 5 carbon atoms per molecule. The so obtained mixture of alcohols is mixed again with the heavy oil in a proportion of, for example, 5 to 25% by weight of alcohols, with respect to the oil, optionally subjected to preliminary desalting, dehydration and separation therefrom of its solid sediments in a conveniently performed desalting operation. A substantially similar process is described in the U.S. Pat. No. 4,027,688 except that, according to this patent, there is not produced a mixture of alcohols from said synthesis gas but essentially methanol; as a matter of fact, the dilution of the heavy oil exclusively with methanol produces an emulsion whose transportion is not sufficiently satisfactory as compared with the emulsion obtained according to the present process, which emulsion is composed of heavy oil and of a mixture of several alcohols in the above-mentioned proportions.

Moreover, a substantial improvement of the present process has for object to make the heavy oils transportable while simultaneously improving their qualities, as far as their utilisation is concerned, by making use, as raw material for synthesizing alcohols, not of the heavy oil itself as withdrawn from the field, but of the fraction of lower value of said oil, i.e. the asphaltenes fraction such as obtained after the deasphalting operation has been performed, by making use of a solvent having at least 5 carbon atoms per molecule and selected particularly from hydrocarbons, for example pentane or a mixture of hydrocarbons containing from 5 to 7 carbon atoms per molecule. A solvent containing less than 5 carbon atoms per molecule would have a too extensive deasphalting effect in the present technological conditions. The advantage of the at least partial deasphalting of the heavy oil consists in the fact that the deasphalted oil already has a very strongly reduced viscosity and the fraction by weight which has to be added thereto to make it transportable is substantially lower than that which would be required in the absence of such deasphalting.

A method, among others, for the production of the desired mixture of methanol and higher alcohols from synthesis gas, consists, for example, of proceeding in a first step, to the synthesis of alcohols containing 1 (or 2) to 10 or 1 (or 2 ) to 5 carbon atoms per molecule and then, in a second step, to the synthesis of methanol in accordance, for example, with the teaching of the U.S. application Ser. No. No. 137,098 filed on Apr. 4, 1980 or of the U.S. Pat. No. 4,122,110.

In accordance with the invention, the mixtures alcohols-deasphalted heavy oil are conveyed to the refining site; on this site it is possible, for example by mere distillation, to separate the gasoline-alcohols mixture distilling below 110° C. from the remainder of the heavy oil; the mixture gasoline-alcohols is used in a fuel pool in admixture with gasoline obtained, for example, by cracking of the distillates or of the deasphalted oils distilling above 350° C. or (and) with gasoline obtained by reforming of the heavy gasoline distilling between 110° and 180° C. More generally, the gasoline-alcohols mixture obtained by distillation may be admixed with gasolines of various origins, obtained from the considered crude oil or from any other crude oil.

An interesting feature of the operation according to the present invention consists in the fact that the heavy oils subjected to the considered refining treatment contain a very low proportion of gasoline; it results therefrom that the mixture of gasoline with alcohols distilling below 110° C. has a high content of alcohols and the Research octane number of this fraction is from 93 to 102 when the proportion of alcohol with respect to the gasoline varies, for example, from 80 to 95% (by weight).

An important feature of the series of process steps forming the object of the invention lies in the fact that the crude oil must be maintained dehydrated so that, when conveyed from the place of production to the refining site, its water content is maintained, for example, lower than 0.3%.

Figure 2:
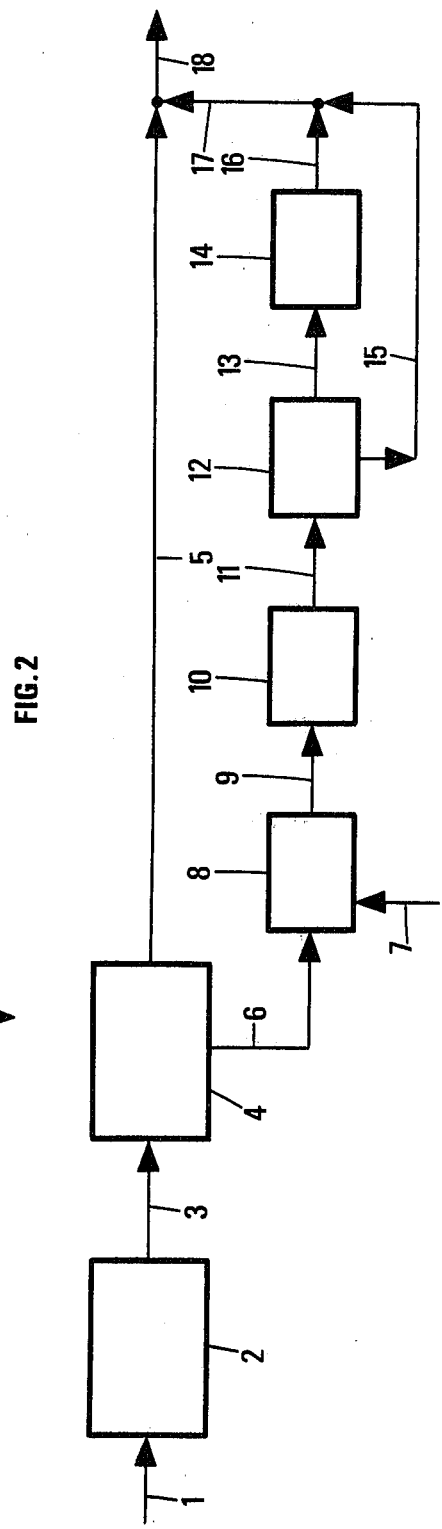
FIG. 2 is a schematic diagram of one embodiment of the process of the present invention.

FIGS. 1 and 2 (one of which illustrates the prior art and the other the invention) give a brief description of the two above explained principles.

In FIG. 1, not conforming with the invention, the crude oil issued from line 1 is conveyed, through line 2, to the desalting unit 3 where sediments, salt and water are removed and discharged through line 4; as the considered charge is a heavy oil of high viscosity, it is generally convenient (and this is also true for the process according to the invention) to admix to the oil, before desalting, a hydrocarbon fraction of low viscosity, so that water settling is achieved under favorable conditions. The considered admixed fraction may be gasoline, straight-run gas oil or a mixture of these two fractions obtained from the crude oil itself and which is partly recycled. The sediments, salts and water are thus withdrawn through line 4 and the salt-free oil is withdrawn through line 5.

An oil fraction is conveyed through line 6 and there is produced, in zone 7, optionally in the presence of oxygen fed through line 8, a synthesis gas which is supplied through line 9 to the methanol production zone 10. The produced methanol is conveyed through line 11 and admixed with the heavy oil of line 5, so as to form the desired heavy oil-methanol mixture, in line 12.

FIG. 2 illustrates the process conforming to the invention, characterized in that it comprises a deasphalting operation and in that the alcohols are obtained from the less noble fraction, i.e. the asphaltenes.

The heavy oil, fed through line 1, is freed from salt in 2, then conveyed through line 3 to zone 4 where it is at least partly deasphalted. The salt removal operation, in view of the viscosity of the oils to which the invention is more particularly applied, is advantageously conducted after admixture with a lighter hydrocarbon solvent as mentioned in the case of FIG. 1. An advantageous option may consist of making use, as "fluxing" agent in the salt removal operation, of the solvent already used for the precipitation of the asphalts in the deasphalting operation, i.e. for example a hydrocarbon (preferably a hydrocarbon having 5 carbon atoms per molecule) or a mixture of hydrocarbons comprising from 5 to 7 carbon atoms per molecule.

The products of the deasphalting operation consist of a deasphalted oil, discharged through line 5, and asphaltenes, discharged through line 6. Optionally, it is possible, in some cases, to remove the solvent, or a portion thereof, from the deasphalted oil withdrawn through line 5. The precipitated asphaltenes are gasified in zone 8, for example by partial oxidation with oxygen introduced through line 7; the obtained synthesis gas ($H_2$, CO and/or $CO_2$) is introduced through line 9 into the optional purification zone 10; then it is fed, through line 11, for example according to a non limitative mode of operation, to zone 12 of synthesis of $C_2$–$C_{10}$ higher alcohols or of $C_1$–$C_{10}$ alcohols and then, through line 13 it is fed to zone 14 for methanol synthesis. After dehydration, the higher alcohols, through line 15, and methanol, through line 16, are admixed before being reinjected, through line 17 into the deasphalted heavy oil, to form the desired heavy oil-alcohols mixture, which can be transported through line 18, as such.

What is claimed is:

1. A process for reducing the viscosity of a heavy oil, comprising the steps of:
   (a) deasphalting at least a portion of the heavy oil, and separately recovering a deasphalted heavy oil and asphaltenes;
   (b) gasifying at least a portion of said asphaltenes to produce a synthesis gas;
   (c) converting at least a portion of said synthesis gas to a mixture of alcohols consisting of methanol and at least one $C_{2-10}$ alcohol; and
   (d) admixing said alcohol mixture with the nondeasphalted heavy oil portion or with the deasphalted heavy oil or with a mixture thereof, to produce an oil of lower viscosity.

2. A process according to claim 1, wherein the heavy oil is at least partly subjected to desalting, dehydration and separation of the solid sediments therefrom before deasphalting of at least a portion thereof.

3. A process according to claim 2 wherein the salt removal is performed by means of a fluxing agent consisting of at least a portion of the deasphalting solvent.

4. A process according to claim 2 wherein the deasphalting solvent consists essentially of a hydrocarbon having 5 carbon atoms per molecule.

5. A process according to claim 2, wherein the mixture of alcohols contains, by weight, about 60 to 85% of methanol.

6. A process according to claim 2, wherein the mixture of alcohols contains, by weight, from 10 to 50% of methanol.

7. A process according to claim 2, wherein the mixture of alcohols contains, by weight, 15 to 40% of methanol.

8. A process according to claim 1, wherein said oil of reduced viscosity contains, by weight, about 5 to 25% of said mixture of alcohols.

9. A process according to claim 1, wherein said heavy oil has a viscosity at 70° C. of close to or higher than 1000 centistokes.

10. A process according to claim 2, step (c) comprising feeding synthesis gas to a first zone for synthesizing:
  (i) methanol and at least one $C_{2-10}$ alcohol or
  (ii) substantially only at least one $C_{2-10}$ alcohol; and then feeding residual synthesis gas from said first zone to a second zone for methanol synthesis, and combining resultant alcohols from said first and second zones to form said alcohol mixture.

11. A process according to claim 9, wherein the resultant oil of lower viscosity is transported through a pipeline.

12. A process according to claim 1, wherein in step (c), the alcohols other than methanol produced from said synthesis gas are $C_{2-5}$ alcohols.

13. A process according to claim 2, wherein in step (d), said alcohol mixture is admixed with the deasphalted heavy oil; and wherein said process further comprises conveying the resultant oil of lower viscosity to a refinery; distilling the oil; and separating the fraction distilling below about 110° C. from the remainder of the heavy oil.

* * * * *